(12) United States Patent
Hussain (10) Patent No.: US 8,761,885 B2
(45) Date of Patent: Jun. 24, 2014

(54) BATTERY LIFE ESTIMATION BASED ON VOLTAGE DEPLETION RATE

(75) Inventor: Saadat Hussain, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 90 days.

(21) Appl. No.: 13/098,141

(22) Filed: Apr. 29, 2011

(65) Prior Publication Data

US 2012/0277832 A1    Nov. 1, 2012

(51) Int. Cl.
*A61N 1/378* (2006.01)

(52) U.S. Cl.
USPC ............................................. 607/29

(58) Field of Classification Search
USPC ............................................. 607/29
See application file for complete search history.

(56) References Cited

U.S. PATENT DOCUMENTS

| | | |
|---|---|---|
| 3,796,221 A | 3/1974 | Hagfors |
| 4,324,251 A | 4/1982 | Mann |
| 4,488,555 A | 12/1984 | Imran |
| 4,556,061 A | 12/1985 | Barreras |
| 4,686,990 A | 8/1987 | Moberg |
| 4,702,254 A | 10/1987 | Zabara |
| 4,715,381 A | 12/1987 | Moberg |
| 4,850,356 A | 7/1989 | Heath |
| 4,867,164 A | 9/1989 | Zabara |
| 4,899,750 A | 2/1990 | Ekwall |
| 4,964,407 A | 10/1990 | Baker et al. |
| 5,025,807 A | 6/1991 | Zabara |
| 5,127,404 A | 7/1992 | Wyborny et al. |
| 5,137,020 A | 8/1992 | Wayne et al. |
| 5,137,021 A | 8/1992 | Wayne et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,188,104 A | 2/1993 | Wernicke et al. |
| 5,193,538 A | 3/1993 | Ekwall |
| 5,201,808 A | 4/1993 | Steinhaus et al. |
| 5,201,865 A | 4/1993 | Kuehn |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,515 A | 7/1994 | Rutecki et al. |

(Continued)

FOREIGN PATENT DOCUMENTS

| | | |
|---|---|---|
| WO | 0108749 | 2/2001 |
| WO | 2004075982 | 9/2004 |

OTHER PUBLICATIONS

International Patent Application No. PCT/US2011/061003, International Search Report and Written Opinion dated Jun. 28, 2012, 10 pages.

(Continued)

*Primary Examiner* — Rex R Holmes
(74) *Attorney, Agent, or Firm* — Cyberonics, Inc.

(57) ABSTRACT

Apparatus and methods for estimating the remaining life of a battery in an implantable medical device ("IMD") are disclosed herein. The terminal voltage of the battery is measured and the measurements create a baseline curve of the battery voltage depletion. The points along the baseline curve can be linearly extrapolated to calculate the voltage depletion rate, which can estimate the remaining life of the battery.

22 Claims, 7 Drawing Sheets

(56) References Cited

U.S. PATENT DOCUMENTS

| | | | |
|---|---|---|---|
| 5,335,657 | A | 8/1994 | Terry, Jr. et al. |
| 5,344,431 | A | 9/1994 | Merritt et al. |
| 5,352,968 | A | 10/1994 | Reni et al. |
| 5,372,607 | A | 12/1994 | Stone et al. |
| 5,391,193 | A * | 2/1995 | Thompson ............. 607/29 |
| 5,431,692 | A | 7/1995 | Hansen et al. |
| 5,458,624 | A | 10/1995 | Renirie et al. |
| 5,496,353 | A | 3/1996 | Grandjean et al. |
| 5,507,786 | A | 4/1996 | Morgan et al. |
| 5,522,865 | A | 6/1996 | Schulman et al. |
| 5,534,018 | A | 7/1996 | Wahlstrand et al. |
| 5,540,730 | A | 7/1996 | Terry, Jr. et al. |
| 5,540,734 | A | 7/1996 | Zabara |
| 5,549,646 | A | 8/1996 | Katz et al. |
| 5,571,150 | A | 11/1996 | Wernicke et al. |
| 5,620,474 | A | 4/1997 | Koopman |
| 5,703,469 | A | 12/1997 | Kinoshita |
| 5,707,400 | A | 1/1998 | Terry, Jr. et al. |
| 5,713,936 | A | 2/1998 | Staub |
| 5,741,307 | A | 4/1998 | Kroll |
| 5,741,311 | A | 4/1998 | McVenes et al. |
| 5,744,931 | A * | 4/1998 | Arai et al. ............. 320/149 |
| 5,755,742 | A | 5/1998 | Schuelke et al. |
| 5,769,873 | A | 6/1998 | Zadeh |
| 5,814,088 | A | 9/1998 | Paul et al. |
| 5,876,425 | A | 3/1999 | Gord et al. |
| 5,891,179 | A | 4/1999 | Er et al. |
| 5,897,577 | A | 4/1999 | Cinibis et al. |
| 5,925,068 | A | 7/1999 | Kroll |
| 5,928,272 | A | 7/1999 | Adkins et al. |
| 6,016,448 | A | 1/2000 | Busacker et al. |
| 6,073,050 | A | 6/2000 | Griffith |
| 6,108,579 | A | 8/2000 | Snell et al. |
| 6,148,235 | A | 11/2000 | Kuiper |
| 6,167,309 | A | 12/2000 | Lyden |
| 6,181,969 | B1 | 1/2001 | Gord |
| 6,185,461 | B1 | 2/2001 | Er |
| 6,212,431 | B1 | 4/2001 | Hahn et al. |
| 6,317,633 | B1 | 11/2001 | Jorgenson et al. |
| 6,341,236 | B1 | 1/2002 | Osorio et al. |
| 6,400,988 | B1 | 6/2002 | Gurewitsch |
| 6,445,951 | B1 | 9/2002 | Mouchawar |
| 6,453,198 | B1 | 9/2002 | Torgerson et al. |
| 6,473,644 | B1 | 10/2002 | Terry, Jr. et al. |
| 6,490,484 | B2 | 12/2002 | Dooley et al. |
| 6,490,486 | B1 | 12/2002 | Bradley |
| 6,553,263 | B1 | 4/2003 | Meadows et al. |
| 6,587,719 | B1 | 7/2003 | Barrett et al. |
| 6,587,727 | B2 | 7/2003 | Osorio et al. |
| 6,609,025 | B2 | 8/2003 | Barrett et al. |
| 6,620,186 | B2 | 9/2003 | Saphon et al. |
| 6,622,038 | B2 | 9/2003 | Barrett et al. |
| 6,622,041 | B2 | 9/2003 | Terry, Jr. et al. |
| 6,622,047 | B2 | 9/2003 | Barrett et al. |
| 6,631,293 | B2 | 10/2003 | Lyden |
| 6,648,823 | B2 | 11/2003 | Thompson |
| 6,654,640 | B2 | 11/2003 | Lyden |
| 6,658,294 | B1 | 12/2003 | Zadeh et al. |
| 6,662,053 | B2 | 12/2003 | Borkan |
| 6,671,552 | B2 | 12/2003 | Merritt et al. |
| 6,671,556 | B2 | 12/2003 | Osorio et al. |
| 6,687,538 | B1 | 2/2004 | Hrdlicka et al. |
| 6,721,600 | B2 | 4/2004 | Jorgenson et al. |
| 6,745,077 | B1 | 6/2004 | Griffith et al. |
| 6,748,273 | B1 | 6/2004 | Obel et al. |
| 6,760,624 | B2 | 7/2004 | Anderson et al. |
| 6,760,625 | B1 | 7/2004 | Kroll |
| 6,804,557 | B1 | 10/2004 | Kroll |
| 6,820,019 | B1 | 11/2004 | Kelly et al. |
| 6,901,293 | B2 | 5/2005 | Rogers et al. |
| 6,940,255 | B2 | 9/2005 | Loch |
| 7,142,923 | B2 | 11/2006 | North et al. |
| 7,254,444 | B2 | 8/2007 | Moore et al. |
| 7,751,891 | B2 | 7/2010 | Armstrong et al. |
| 7,904,161 | B2 | 3/2011 | Osypka |
| 2002/0013613 | A1 * | 1/2002 | Haller et al. ............. 607/60 |
| 2003/0065366 | A1 * | 4/2003 | Merritt et al. ............. 607/27 |
| 2004/0039424 | A1 * | 2/2004 | Merritt et al. ............. 607/29 |
| 2006/0025829 | A1 * | 2/2006 | Armstrong et al. ............. 607/29 |
| 2007/0150019 | A1 | 6/2007 | Youker |
| 2007/0179548 | A1 * | 8/2007 | Armstrong et al. ............. 607/29 |
| 2007/0216366 | A1 | 9/2007 | Inamine |
| 2008/0097544 | A1 * | 4/2008 | Gandhi et al. ............. 607/29 |
| 2012/0197341 | A1 * | 8/2012 | Cowley et al. ............. 607/45 |

OTHER PUBLICATIONS

Terry, R.S., et al., "The Implantable Neurocybernetic Prosthesis System," Pacing and Clinical Electrophysiology, vol. 14, No. 1, (Jan. 1991), pp. 86-93.

Woodbury, J.W. et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

International Application No. PCT/US2007/000337, Written Opinion dated Jul. 27, 2008, 8 pgs.

International Application No. PCT/US2005/026514, Written Opinion dated Oct. 10, 2006, 4 pgs.

* cited by examiner

BATTERY LIFE ESTIMATION BASED ON VOLTAGE DEPLETION RATE

BACKGROUND OF THE INVENTION

1. Field of the Invention

The present disclosure generally relates to rechargeable battery systems. More particularly, the present disclosure relates to a method for estimating remaining battery capacity using an algorithm based on battery terminal voltage.

2. Description of the Related Art

In recent years there has been an explosion in the popularity and types of portable electronic devices. Such devices include communication and entertainment devices, such as cell phones, PDA's, portable music and video players and the like, as well as electronic devices that are implantable into a human or animal body, such as pacemakers, implantable drug delivery systems and nerve stimulation devices. These and other types of portable electronic devices generally rely upon electrochemical storage batteries as a power source. Many of these devices use rechargeable batteries, while others use conventional single-use batteries. In either case, however, it can be desirable to have an accurate estimate of remaining battery capacity or battery life in order to know when to recharge or replace the batteries. This is particularly true in the case of implantable electronic devices, where the health of the user may depend upon proper functioning of the device, and the device is not easily accessible, since replacing a battery requires an invasive surgical procedure.

There are various known methods for estimating remaining battery life in electronic devices that are currently used. For example, methods that have been adopted to predict or estimate remaining battery life include the remaining capacity (mAh) method, direct energy computation (J), and the coulomb counter (Amps/s) method. Unfortunately, many of these methods rely upon some significant and sometimes inaccurate assumptions, can be moderately to highly complex to implement, and the accuracy of these methods varies widely. Ironically, some battery life estimation methods that are currently used are computationally intensive, such that they impose a substantial strain on battery life in the course of computing battery life and reduce overall system efficiency.

The present disclosure is directed to overcoming, or at least reducing the effects, of one or more of the issues set forth above.

SUMMARY OF THE INVENTION

It has been recognized that it would be advantageous to develop a simple and robust method for estimating remaining battery capacity in an electronic device.

It has also been recognized that it would be advantageous to develop a method for estimating remaining battery capacity in an electronic device that uses only minimal power from the electronic device itself In accordance with one aspect thereof, the present disclosure provides a method for managing a battery powering an implantable medical device (IMB) comprising taking a plurality of regular, periodic terminal voltage readings of the battery in the IMD and estimating future battery performance characteristics based upon a linear extrapolation from the plurality of voltage readings. The performance characteristics may include at least one of time to depletion of the battery and time to end of service of the battery.

The method may further comprise obtaining a baseline curve of voltage depletion over time for the battery in the IMD under selected operating parameters and making a first estimate of future battery performance characteristics based upon a linear extrapolation from the plurality of voltage readings and an initial point of the baseline curve. The method may further comprise modifying the baseline curve based upon a change of the operating parameters of the IMD. The method may further comprise wirelessly transmitting data representing the detected terminal voltage of the battery from the IMD to a remote computing device. The IMD may be an implantable pulse generator for vagus nerve stimulation.

The IMD may take the plurality of regular, periodic terminal voltage readings and a remote computing device may estimate the future battery performance characteristics. The remote computing device may be a PDA, smartphone, laptop computer, or a special purpose portable computing device. The method may further comprise providing to a user of the IMD an indication of the future battery performance characteristics. The indication may be an indicator light, an alphanumeric display, an iconic indicator, or an audible indicator.

In accordance with yet another aspect thereof, the present disclosure provides a method of estimating a life of a battery in an implantable medical device (IMD). The method comprising obtaining a baseline curve of voltage depletion over time for the battery in the IMD under selected operating parameters, taking a first reading and subsequent readings of battery terminal voltage at regular intervals, making a first battery life estimate based upon a linear extrapolation from the first voltage reading and the baseline curve, and making subsequent battery life estimates based upon a linear extrapolation of the subsequent voltage readings.

The battery life estimate may include time to depletion of the battery and/or time to end of service of the battery. The regular interval for taking readings of the battery terminal voltage may be about once per day. The method may further comprise providing to a user an indication of the first or subsequent battery life estimates using an indicator. The indicator may be an indicator light, an alphanumeric display, an iconic, indicator, audible indicator, or equivalent device. The method may further comprise wirelessly transmitting data representing the voltage readings from the IMD to a remote computing device, with the IMD taking the first and subsequent reading of battery terminal voltage and the remote computing device performing the first and subsequent battery life estimates.

In accordance with yet another aspect thereof, the present disclosure provides an implantable system comprising an implantable device having a microprocessor, system memory, a battery, and a battery circuit capable of measuring battery terminal voltage. The system comprises an external computing device having a microprocessor and system memory and a computer program product. The computer program product being stored in the system memory of the implantable device or the external computing device. The computer program product comprising machine-readable instructions for periodically measuring terminal voltage of the battery and estimating a life of the battery based upon a linear extrapolation from the plurality of the periodic voltage measurements.

The system memory may include data representing a baseline curve of voltage depletion over time for the battery in the implantable device under selected operating parameters and the computer program product may include instructions for making a first estimate of the life of the battery based upon the baseline curve and first of the periodic voltage measurements. The implantable device may further comprise a wireless transmitter and programming instructions for periodically measuring terminal voltage of the battery and transmitting data representative thereof to the external device.

These and other embodiments of the present application will be discussed more fully in the description. The features, functions, and advantages can be achieved independently in various embodiments of the claimed invention, or may be combined in yet other embodiments.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

DESCRIPTION OF ILLUSTRATIVE EMBODIMENTS

Illustrative embodiments are described below as they might be employed in a method for estimating battery capacity. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

As used herein, the term "implantable" means a device that can be completely implanted into a human or animal body, with no portions of the apparatus extending outside the body after implantation.

As used herein, the terms "implantable device" and "implantable medical device" or "IMD" mean any type of electrical device that is implantable into a human or animal body, and is configured to monitor or affect a function of the body. Examples of implantable medical devices include cardiac pacemakers, nerve stimulation devices, and implantable drug delivery devices.

As noted above, there are a variety of battery powered devices in which it is desirable to have an accurate estimate of remaining battery power. In addition to communication and entertainment devices, this includes implantable devices that can be used for monitoring and affecting physiological or biological function of a human or animal body. Such devices include cardiac pacemakers, implantable drug delivery systems and nerve stimulation devices. Among the latter are implantable devices for vagus nerve stimulation (VNS). VNS was approved by the FDA in 1998 as an adjunctive therapy for epilepsy with partial onset seizures. VNS is achieved through an implanted pulse generator that delivers a bipolar, biphasic pulse to the vagus nerve. The implant procedure is very similar to the implantation of a pacemaker. The generator is implanted subcutaneously, typically in the upper left pectoral region. An electric lead is connected between the pulse generator and one or more electrodes that are attached to the vagus nerve. While the following description presents a system and method for estimating battery life in the context of an implantable vagus nerve stimulation system, this application is only exemplary. It is to be understood that the system and method disclosed herein can be applied to a wide variety of battery-powered electronic devices, and is not limited to the particular exemplary application in which it is shown and described.

Figure 1:
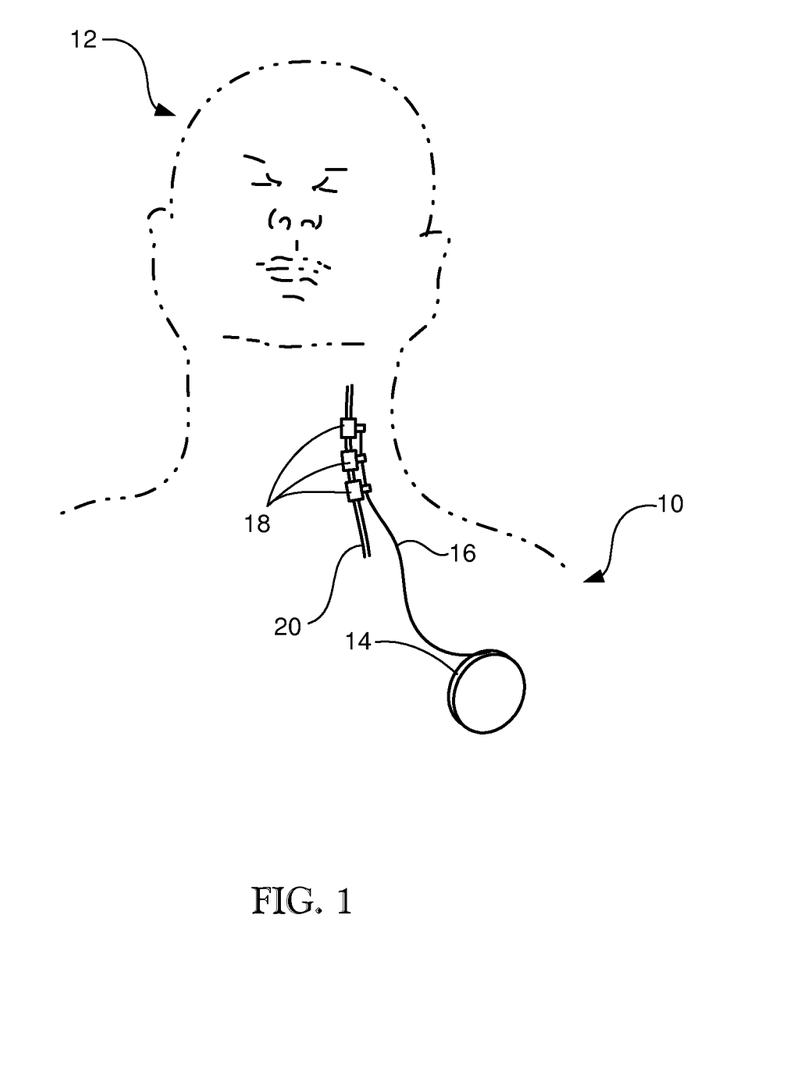
FIG. 1 is a schematic representation of a human subject showing a subcutaneous vagus nerve stimulation system, having a lead extending from a battery-powered pulse generator device to electrodes attached at the left vagus nerve.

Shown in FIG. 1 is a schematic diagram of one embodiment of an implantable VNS system, indicated generally at 10, implanted into a patient 12. The system includes an implantable pulse generator ("IPG") 14, and lead 16 that includes one or more electrodes 18 located at the distal end of a tether. The tether and electrodes 18 are collectively referred to as the lead 16, and the lead provides an interface between the pulse generator 14 and the electrodes 18. The electrodes 18 are attachable to the vagus nerve 20. An implantable VNS system of this type and having these basic features is known to those of skill in the art, and is commercially available, such as from Cyberonics, Inc. of Houston, Texas.

The pulse generator 14 can be a multi-programmable device, which allows a physician to set various parameters of operation of the device. The programmable parameters can include signal amplitude (e.g., 0-3.5 mA), frequency (e.g., 1-30 Hz), pulse width (e.g., 130-1000 μs), signal ON time (e.g., 7-60 sec) and signal OFF time (e.g., 0.2-180 min). It is to be appreciated that these pulse parameters are only exemplary, and that other parameters can also be used. The pulses can be delivered at the specified amplitude and frequency over the course of the ON time, and then during the OFF time, no stimulation takes place. This type of device typically does not stimulate continuously because it has been found that the antiepileptic effect tends to last much longer than the actual time of stimulation. In one embodiment, pulse settings can be 2 mA, at 15 Hz frequency, 250 µs pulse width, with a 30 sec ON time, and 5 min OFF time. The variability in parameters allows the physician to adjust for greater efficacy or less severe side effects, depending on the patient.

Figure 2:
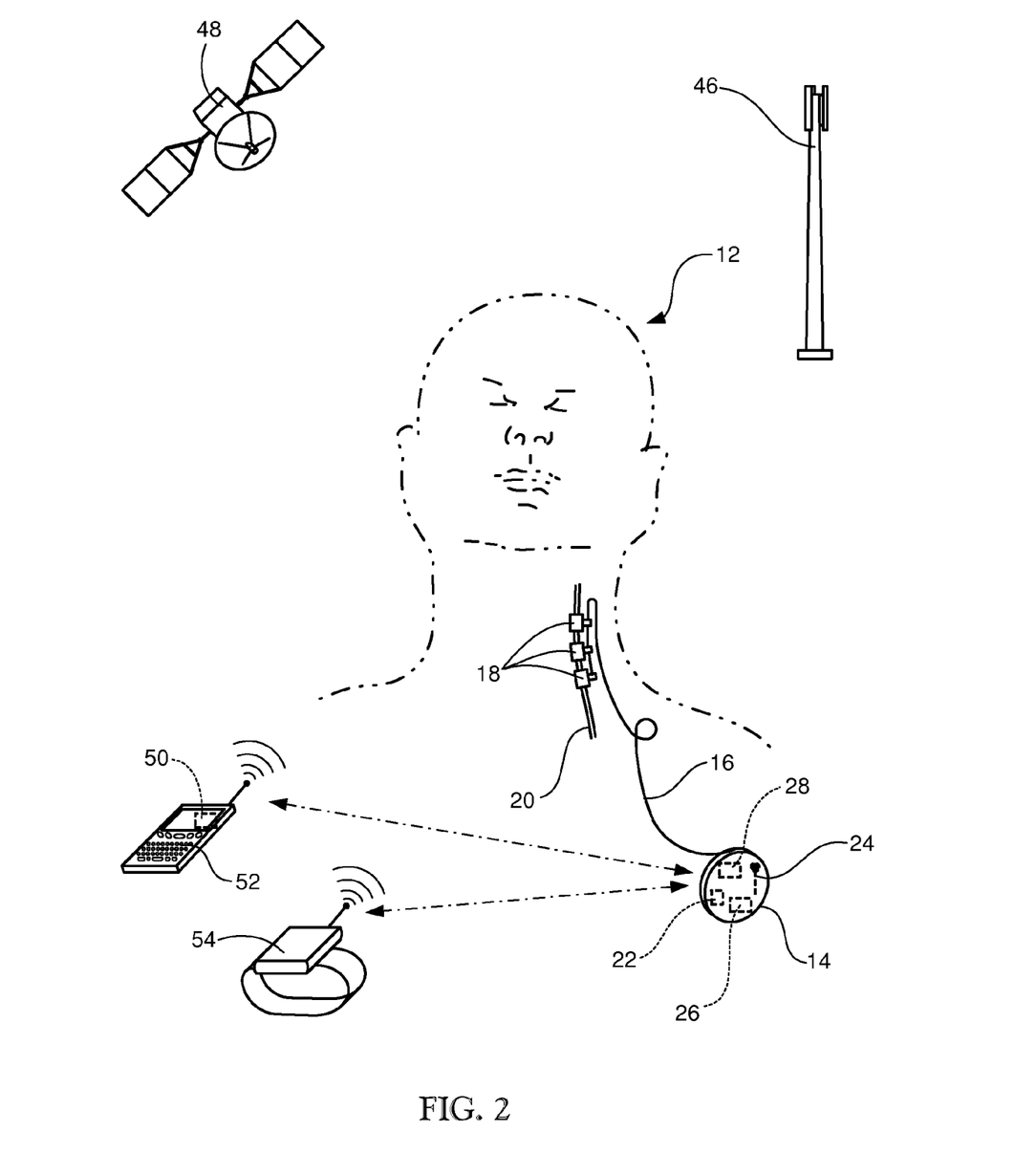
FIG. 2 is a schematic representation of a portion of a battery-powered implantable pulse generator device and a remote handheld computer device in wireless communication with the pulse generator device and configured to compute an estimate of remaining battery capacity in the pulse generator device.

As shown in FIG. 2, the pulse generator 14 can include within its housing a variety of components, including battery 22, an antenna 24, a GPS transceiver 26, and a microprocessor 28 with digital memory. The battery 22 can be a rechargeable battery, and can be configured for periodic inductive recharging. While the components of a recharging system are not specifically shown herein, an exemplary recharging system may include a recharging power source worn outside the patient's body, which includes a primary coil designed to inductively couple to a secondary coil implanted in the body and connected to battery 22. Power is transferred from the primary coil to the secondary coil and stored in the battery 22. Recharging sessions may occur daily, weekly, monthly, or some other frequency depending on the capacity of battery 22 and the rate of energy consumption of the electronics powered by battery 22. The general concepts of a rechargeable battery 22 used in an implantable device 14 are widely known but utilized infrequently because it is technically difficult to design and introduces more risks when patients fail to comply with the prescribed regimen for the recharging session. The antenna 24 is a common element for an implantable device 14, and can be provided to send and/or receive data and programming and control instructions from an external communications device, as discussed below. This allows the implanted device 14 to receive programming and control instructions from an external communications device, and to transmit data regarding operation of the pulse generation device. Communications and control with implanted devices is well known and widely used. Devices such as pacemakers and the like are routinely programmed and/or controlled via wireless communication methods, such as the Medical Information Communication System protocol (MICS), which uses radio waves to transmit information to and from implanted devices.

Figure 3:
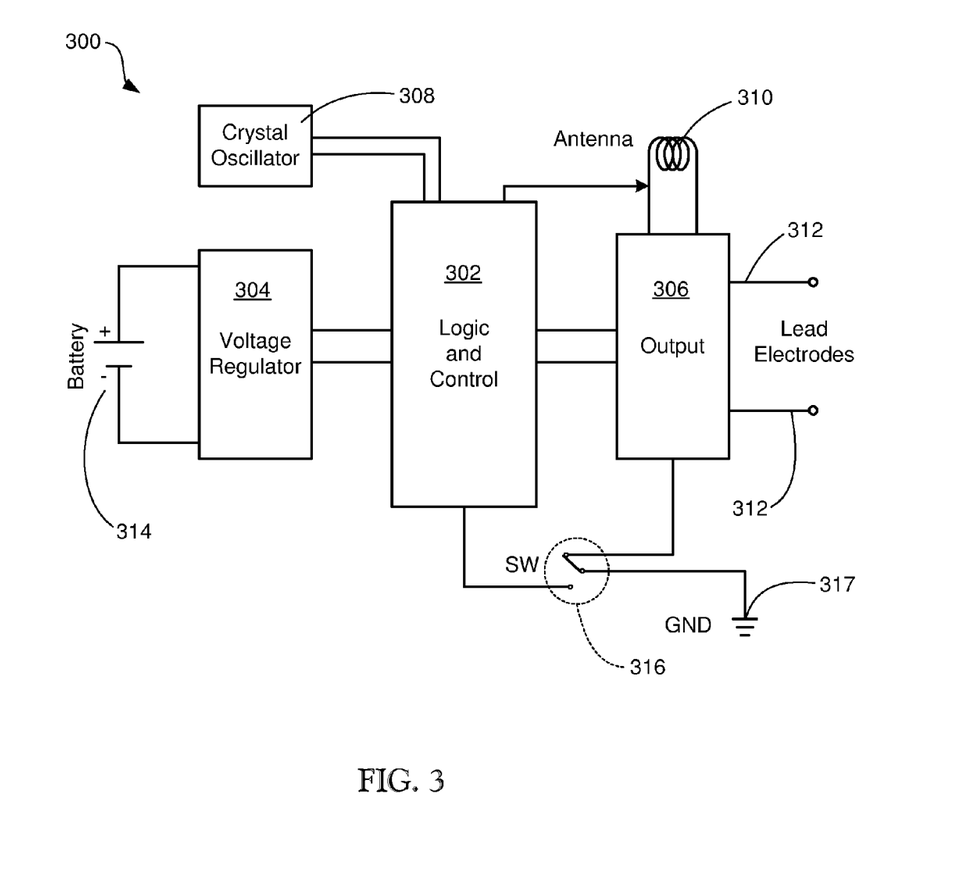
FIG. 3 is a schematic diagram of the internal components of an embodiment of an implantable pulse generator for a VNS system.

A more specific schematic diagram of the internal components of an embodiment of an implantable pulse generator device, indicated generally at 300, is shown in FIG. 3. In this embodiment the pulse generator device includes a logic and control unit 302, a voltage regulator unit 304, an output unit 306 and a crystal oscillator 308. The logic and control unit 302 contains circuitry and programming for control and operation of the pulse generator device, along with digital memory for storing programming instructions. The logic and control unit is operatively coupled to an antenna 310, which allows programming and operational data to be transmitted and received by the pulse generator device. The antenna 310 is driven by the output unit 306, which also directly provides nerve stimulation signals via the lead electrodes 312.

Also operatively connected to the logic and control unit 302 are the crystal oscillator 308 and the voltage regulator 304. The crystal oscillator 308 provides an accurate time signal for the logic and control unit 302. The voltage regulator 304 controls power input from the battery 314 to the logic and control unit. The pulse generator can also include a reed switch 316 that allows selective connection of the logic and control unit 302 or output unit 306 to ground 317. This allows the pulse generator device 300 to operate in a secondary magnet mode, delivering a pre-programmed burst of stimulation when activated by an external magnet (e.g., a permanent magnet worn on the patient's wrist and swiped over switch 316 to activate the secondary mode of operation). While the elements shown in FIG. 3 are illustrated as hardware elements, it is to be recognized and understood that many portions of the pulse generator device can be implemented as firmware, software or the like, and that many combinations are possible.

While a GPS transceiver (26 in FIG. 2) can be incorporated as a specific hardware element in the implanted pulse generation device 14, one of skill in the art will recognize that GPS functions can be programmed into the logic and control unit 302. As another alternative, a GPS transceiver and/or corresponding programming can be placed in other locations associated with a patient's body. For example, referring back to FIG. 2, a GPS transceiver 50 can be associated with an external PDA or smart phone-type device 52, or a wristwatch or wristwatch-like device 54, or some other external computing device. Other types of wearable or external computing devices can also be used, such as a Pocket PC®, i-Phone®, a laptop computer, a special purpose portable computing device, etc. The wristwatch-like device 54 can be considered as one example of a special purpose portable computing device. The external device can function as an activation or input/output device for the implanted device 14. As such it can incorporate an output mechanism for providing indications to the user of aspects of operation of the implanted device 14 (e.g. operational parameters, errors, battery condition, responding to seizure detections, etc.). The output mechanism can provide indications such as indicator lights, alphanumeric indications, icons, audible alerts, etc. The implanted device 14 itself can also include an output mechanism in the form of an audible alert which can be heard outside the body. Such an alert can be useful for noting error conditions, battery depletion, etc.

The smart phone 52 and wristwatch device 54 are shown in FIG. 2 with antennas, which are intended to represent the wireless communications capability of the devices, rather than the shape or position of an actual antenna structure. The antenna allows the external device to receive signals from a cellular or other mobile telephone system, represented by the cellular tower 46, or from satellites 48, or other communications system. The external device can be configured to transmit data to the pulse generation device 14 using Bluetooth or some other wireless transmission protocol, for example.

Performing various computational operations and/or having various hardware components included within a device other than the pulse generation device 14 can be desirable for power conservation. For example, power-hungry microprocessing tasks and analysis can be transferred to the external device, rather than being performed by the microprocessor 28 of the pulse generation device 14, with the results of those microprocessing tasks transmitted back to the implanted device 14. This can conserve power for the implanted device 14. Similarly, having an external GPS transceiver and associated microprocessor can also reduce power demands on the implanted pulse generator 14. A GPS transceiver that is in substantially constant communication with a GPS satellite system and a microprocessor that analyzes the positional information can use significant power, which is at a premium with implanted devices.

One microprocessing task that can be performed by an external device in communication with a battery powered device is computation of battery life or estimation of time to depletion or end of service of a battery. As noted above, it is desirable to have an accurate estimate of remaining battery power and battery life for a battery-powered electronic device. This is of particular interest for implanted devices, since the health of the user may depend upon the device, and direct access to the battery generally requires a surgical procedure. Thus, for example, the microprocessor associated with a smart phone 52 or wristwatch device 54 or some other external device can be programmed to receive battery data measurements (e.g. open circuit voltage), transmitted from the pulse generator 14, and perform the analysis to estimate remaining battery life. The external device can then transmit battery information, operational commands or other information to the pulse generation device 14 or some other device.

Advantageously, a method has been developed for more accurately estimating battery capacity and time to battery depletion in an electronic device, such as an implanted pulse generator device like that shown in FIGS. 1-2. When connected in a circuit, the terminal voltage of a battery depends upon several factors, such as the rate of change of chemical reactions in the battery, energy density variations, the rate of internal charge degradation, the rate of battery capacity loss, the rate of change of internal leakage, the state of charge for a given operating point, variation of internal resistance, load variation, rate of discharge, temperature variation, etc. While many of these factors are difficult to measure or compute directly and accurately, voltage can be directly measured with high accuracy. Advantageously, where estimating battery capacity is concerned, terminal voltage appears to be a good common denominator in relation to other relevant factors.

The method disclosed herein, based on the battery's voltage depletion rate (VDR) provides a simple implementation, and its estimation gets more accurate over time, especially in the last 25% of the battery's useable life threshold. The method utilizes samples of battery voltage measurement and a lookup table of various voltage load curves. An appropriate load curve can be used for initial base line estimate only, after which direct voltage measurements are used to provide a linear extrapolation to battery depletion. As time passes, the battery voltage measurement determines the VDR of the battery over a given time period, with greater and greater accuracy.

Figure 4:
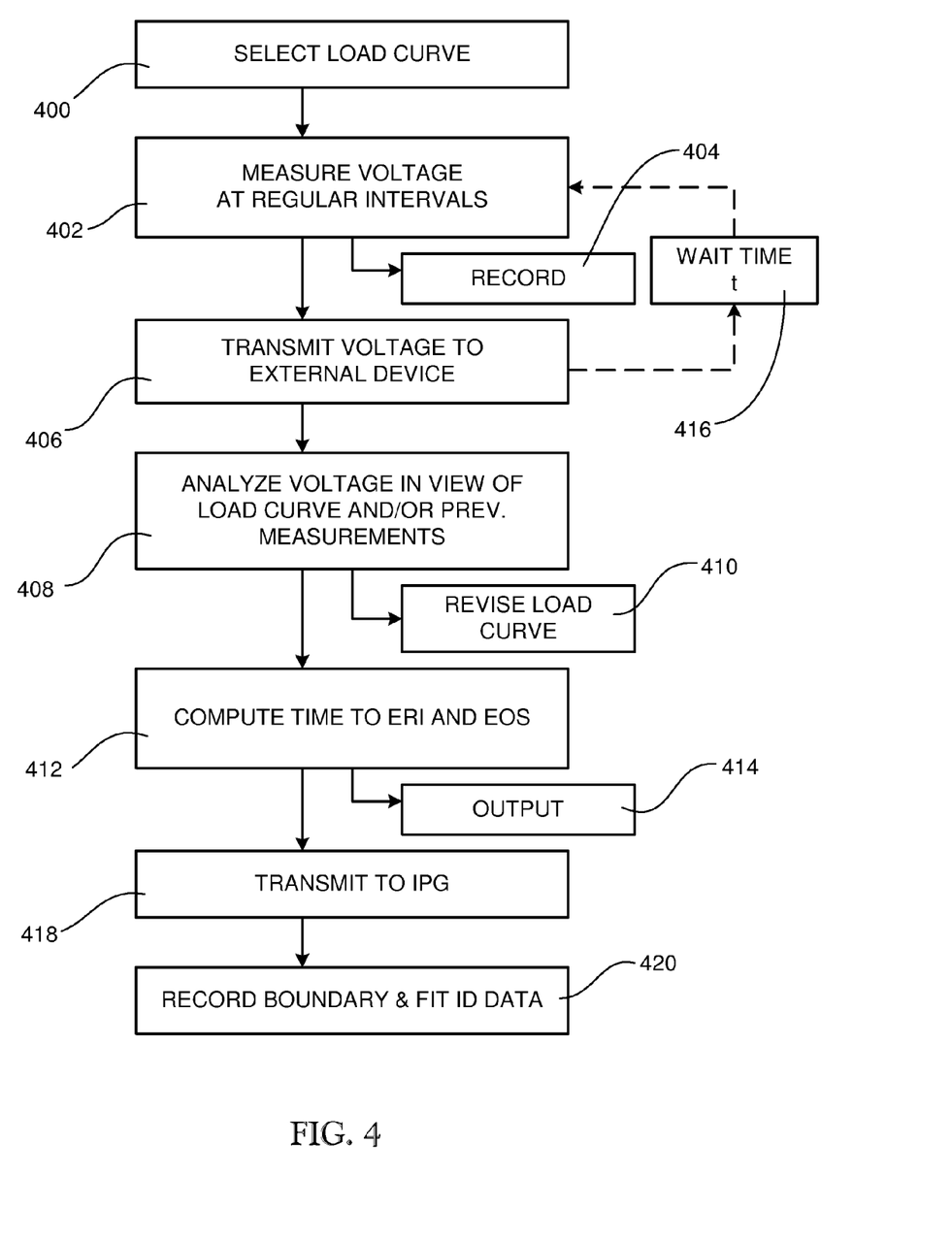
FIG. 4 is a flowchart outlining the steps in one embodiment of a method for estimating battery capacity in accordance with the present disclosure.
Figure 6:
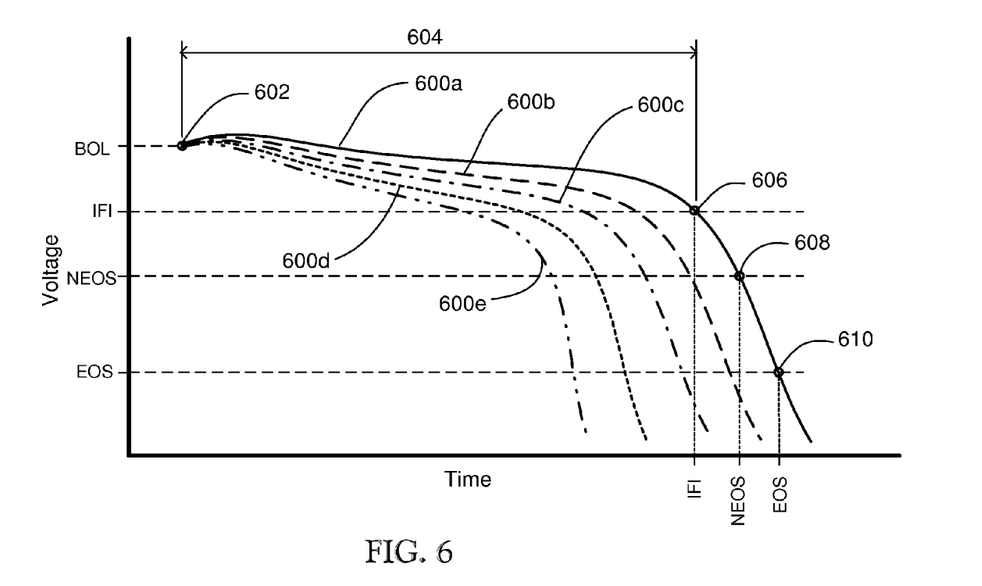
FIG. 6 is a graph providing multiple statistically-derived battery load curves showing voltage versus time for a given battery under various load conditions.

Provided in FIG. 4 is a flowchart outlining the steps in one embodiment of a method for estimating battery capacity in accordance with the present disclosure. As indicated in FIG. 4, the first step in the method is to select or establish a baseline VDR curve (step 400). This curve is a statistically-derived battery load curve of voltage versus time. This is a presumed curve, and is preferably a high confidence (+/−3-Sigma) curve which can be obtained from multiple data sets stored in a lookup table (e.g. in the external device). There are two possible approaches that can be used to establish this curve. The first approach is to extract load curves for all possible load scenarios (e.g., various VNS Therapies). FIG. 6 is a graph providing multiple statistically-derived battery load curves showing voltage versus time for a given battery under various presumed load conditions. For example, curve 600a is a curve showing voltage versus time for a relatively lightly loaded battery, while curve 600e represents the depletion of voltage over time for a higher load upon the battery. Curves 600b-d show load curves for other conditions between these two extremes.

The load curves 600a-e shown in FIG. 6 can be computed based upon presumed battery loading conditions over time. For an implanted pulse generator, for example, the loading conditions can include the resistance of the pulse generator lead (e.g. 3k Ohms), pulse current (e.g. 0.5-3.0 mA), pulse frequency (e.g. 15-30 Hz), pulse duration (e.g. 130-1000 µs), and duty cycle—that is, the percentage of time that pulses are generated (e.g. 10%, 33%, 50%). Based on this information, as well as expected power consumption of the pulse generator microprocessor and other internal circuitry (which can be measured through bench testing) under anticipated operations (e.g. computational operations, data transmission, etc.), an applicable VDR load curve can be computed. This curve can be stored in memory in the implanted device, and/or in an external device.

Figure 7:
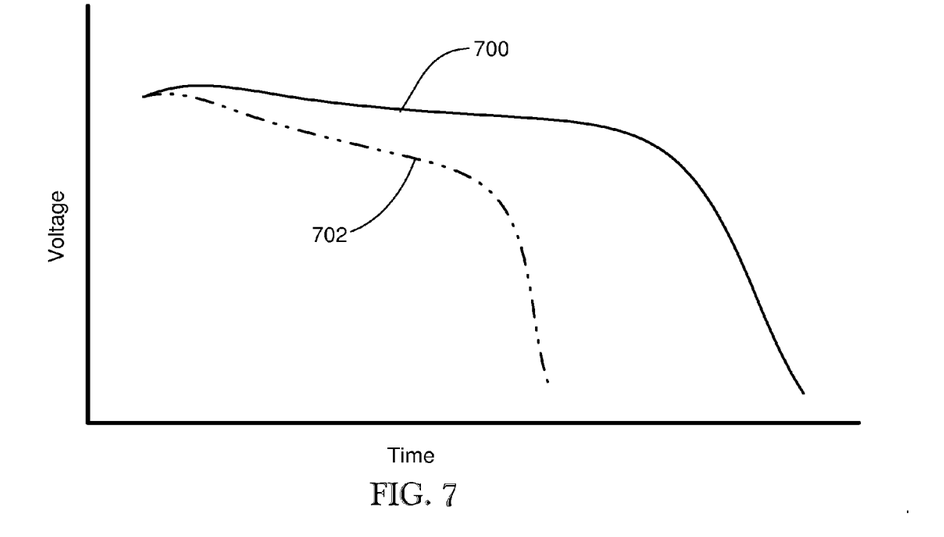
FIG. 7 is a graph showing minimum and maximum statistically-derived battery load curves showing voltage versus time for a given battery under minimum and maximum presumed loads.

A second approach to selecting or establishing a VDR load curve is to extract two boundary load curves, one for the minimum possible load and another for the maximum possible load (the best case and the worst case) that the system is expected ever to experience. This approach is illustrated in the graph of FIG. 7, wherein a top boundary curve 700 is shown, corresponding to the minimum load condition, and a lower boundary curve 702 is shown, corresponding to the maximum load condition. The battery load for these minimum and maximum conditions can be determined based upon anticipated or measured resistance, current, pulse frequency and duration, duty cycle and expected electronics power consumption of the implanted device, in the manner described above. Once the minimum and maximum curves 700, 702 are determined, all operating load points that are between these two curves can be mathematically derived. Alternatively, a curve fitting or estimation operation can be used to derive the additional curves. For example, load points between the curves can be estimated based on the probability of points being near the median rather than the maximum or minimum.

Referring back to FIG. 4, once the presumed load curves are established, the next step in this method is computation of the VDR during operation of the implanted device. This first involves taking periodic measurements of battery terminal voltage (step 402). This is a relatively simple matter for most portable electronic devices, since most such devices include a voltage meter. Consequently, no additional hardware is needed to take this measurement, only suitable software is required in the implanted device. In one embodiment, the battery voltage is measured once per day, though other measurement periods can also be used (e.g., per second, per minute, per hour, etc.). Each voltage measurement can be stored in memory (step 404), if desired. As noted above, it can be desirable to perform various computational operations using an external device, rather than the implanted device. Accordingly, the implanted device can transmit each voltage measurement to an external device (step 406) to allow that device to perform the battery capacity estimation. After transmission, the implanted device can simply wait some time "t" (step 416), depending upon the selected voltage measurement interval, before again measuring voltage at step 402.

Several points of interest are shown on the top line of the graph of FIG. 6, and these points relate to the battery estimation method disclosed herein. The extreme left end of each curve 600a-e represents the condition of the battery at its beginning of life (BOL). At the BOL point 602, the battery will have some initial voltage, which can vary slightly from battery to battery, but is relatively predictable. In one embodiment, the BOL voltage is about 3.0 volt. The initial portion 604 of the voltage depletion curve is relatively linear, and only gradually diminishes until reaching a knee point 606, at which the voltage begins to drop off. The initial, nearly linear portion 604 of the voltage curve can represent anywhere from about 75% to about 90% of the battery's total life. The knee point 606 can be referred to as the intensified follow-up indicator (IFI) point. The exact voltage point for this designation can vary. In one embodiment, with a BOL voltage of 3.0 volt, the IFI voltage is about 2.74 volt, and the remaining battery capacity at this point is about 10%. At the IFI point, a warning message can be displayed (e.g. on an external device) to a user to indicate that the battery of the implanted device has depleted to a level where more frequent clinical monitoring is recommended.

After the IFI point has been crossed, the next point of interest in this embodiment is the near end of service (NEOS) point 608. In one embodiment, this point can represent a voltage of 2.41 volt, with about 5% of remaining battery capacity. Reaching the NEOS point can be viewed as indicating that the battery should be replaced as soon as possible. Again, an indication of NEOS can be provided to a user on an external device. Upon reaching the NEOS point, or at some voltage level thereafter, the implanted device can be programmed to discontinue full functioning, and revert to an energy saving mode, where only essential operations are undertaken to maintain memory, transmit data, or receive data, etc.

The next point of interest is the end of service (EOS) point 610, indicating that the battery's useful life is over (0% remaining capacity). A suitable EOS indication can be provided to an external device. In one embodiment the EOS point 610 represents a voltage of about 2.0 volt. At this point, there is still some charge left in the battery, but the voltage level has become too low to maintain even basic functioning of the implanted device.

Referring back to FIG. 4, the baseline VDR curve that was selected in step 400 provides the first data point for estimating voltage depletion rate. This point is presumably the BOL point 602 in FIG. 6. Once the first voltage measurement is taken (step 402) with the implanted device in operation, that measurement provides a second data point. Having this data allows the system to analyze the voltage in view of the VDR load curve and the measured voltage value (step 408). Specifically, using these two initial values, a linear extrapolation is made to predict the voltage depletion rate.

Given potential errors in the initial assumptions for the voltage depletion curve, it is possible that the initial voltage depletion estimate may have some error. For example, as can be seen in FIG. 6, the initial period of battery use can demonstrate a slight increase in terminal voltage. If the first measured voltage value represents an increase from the initially-presumed voltage level, a linear extrapolation therefrom can appear to suggest that the battery will never die. However, once a second voltage measurement is taken, the initially presumed VDR curve is no longer needed. The load curve is required for the initial baseline estimate only. As time passes, the battery voltage measurement, rather than the curve selected in step 400, determines the VDR of the battery. Future estimates are based solely on the measured battery terminal voltage data. Thus, step 408 is regularly repeated throughout the life of the battery, but is implemented differently for the first voltage measurement than for all the rest. At the first measurement, the battery life is estimated based upon the voltage in view of the selected VDR load curve. Thereafter, the battery life can be estimated, and the VDR curve updated, based solely on the first and subsequent measured voltage values.

Only a few actual voltage measurements are needed to establish a more reliable VDR curve. After each analysis step (step 408), the VDR load curve can be revised (step 410) based on the actual voltage measurements. Based on the linear extrapolation in view of the new voltage measurements, the time to IFI, NEOS, EOS and time to recharge can be estimated (step 412). This new battery life estimate can be provided as output to a user (step 414) and transmitted back to the implanted device, such as an IPG (step 418) if desired. The system can then also record the new boundary and curve fit data (step 420). Output and indications to a user can be provided in a variety of ways. For example, an external device can have an alphanumeric display (e.g. an LCD screen) that provides specific words or indications to a user, including icons indicating different battery conditions. Alternatively, an external device can have indicator lights or audio alerts that provide battery life indications. An audible alert can also be provided by an implanted device itself. Other options can also be used.

Figure 8:
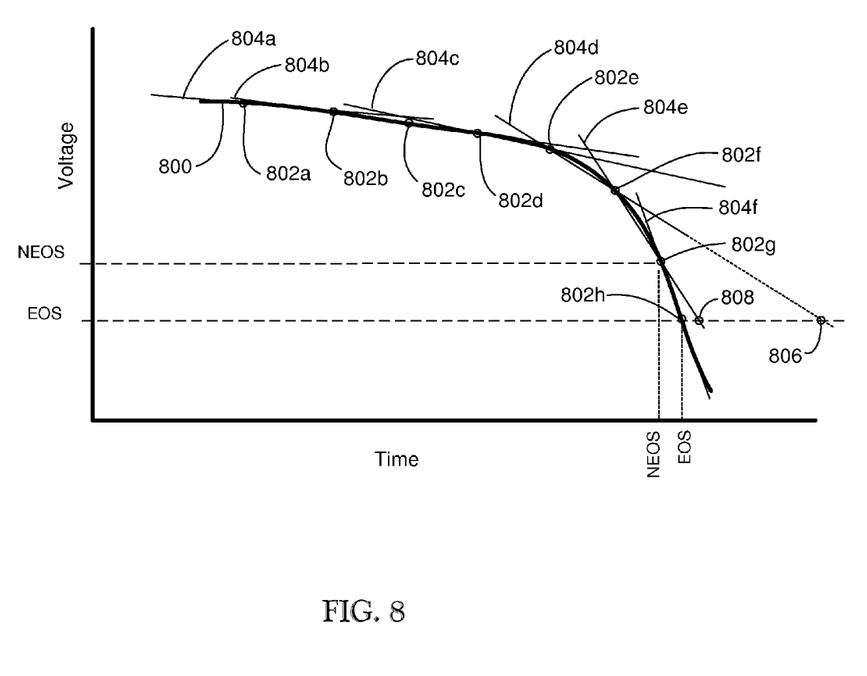
FIG. 8 is a high-resolution portion of one of the graphs of FIG. 6, showing a series of linear fit approximations of the curve based on voltage measurements.

The process of using multiple voltage measurements to produce a linear fit is illustrated in FIG. 8, which provides a high-resolution portion of one of the graphs of FIG. 6. This graph shows a series of linear fit approximations, represented by straight line segments 804*a-f* of the curve 800 based on voltage measurements. Over time, a series of voltage measurements 802*a-h* are taken, and these fall in various places along the curve 800. A linear approximation can be made between any two voltage measurements, and these approximations gradually come closer and closer to predicting the NEOS, EOS, or time to recharge points, as shown. For example, while the linear extrapolation of line 804*d* predicts an EOS time at time point 806, line 804*e*, computed subsequently, more accurately predicts EOS at time point 808.

There are various boundary points that can be used for the linear fit approximation. In one embodiment, these boundary points can correspond to the IFI, NEOS and EOS points shown in FIG. 6. For example, the substantially linear portion 604 of the curve can be referred to as "Fit-1," and correspond to voltage in the range of 3.10V to 3.00V (i.e., between 602 and 606). The next linear fit boundary can be called "Fit-2" and correspond to voltage in the range of 2.99V to 2.85V (i.e., between 606 and 608), and a final boundary "Fit-3" can correspond to voltage in the range of 2.85V to 2.00V (EOS) (i.e., between 608 and 610). In region Fit-1 can be fit or approximated by a mathematical model, but the shape of the curve changes significantly in the regions Fit-2 and Fit-3. Similarly, the Fit-2 region can be fit with a second mathematical model and the Fit-3 region can be fit with a third mathematical model. Other points can also be predicted, if desired.

By using the disclosed linear fit methods, the time required for the battery's terminal voltage to reach a given depleted value can be more accurately predicted. Some aspects of these methods can require care and consideration during application. For example, it has been found that the accuracy of the battery life estimate can decline if the computation of the estimate is done within an hour of the effective change of the load and/or the load parameters. That is, if a physician changes operating parameters of the implanted device (e.g. through wireless transmission of new operating instructions to the implanted device), such as duty cycle, stimulation current, etc., a voltage measurement taken shortly after that sort of change can produce an inaccurate battery life estimate. However, such errors will gradually work themselves out with regular repeated voltage measurements in the subsequent days or weeks. In some embodiments, the system can be programmed to select or establish a new VDR curve as a starting point whenever new operational parameters are initiated. That is, each time operational parameters are changed for the implanted device, the system can revert to step 400 in the process outlined in FIG. 4, and begin as if the battery were at the beginning of its life.

Similarly, if the implanted device is provided with a rechargeable battery, a new VDR curve can be selected or established each time the battery is recharged. A rechargeable battery may have a characteristic VDR curve, which can be analyzed using the methods disclosed herein.

Figure 5:
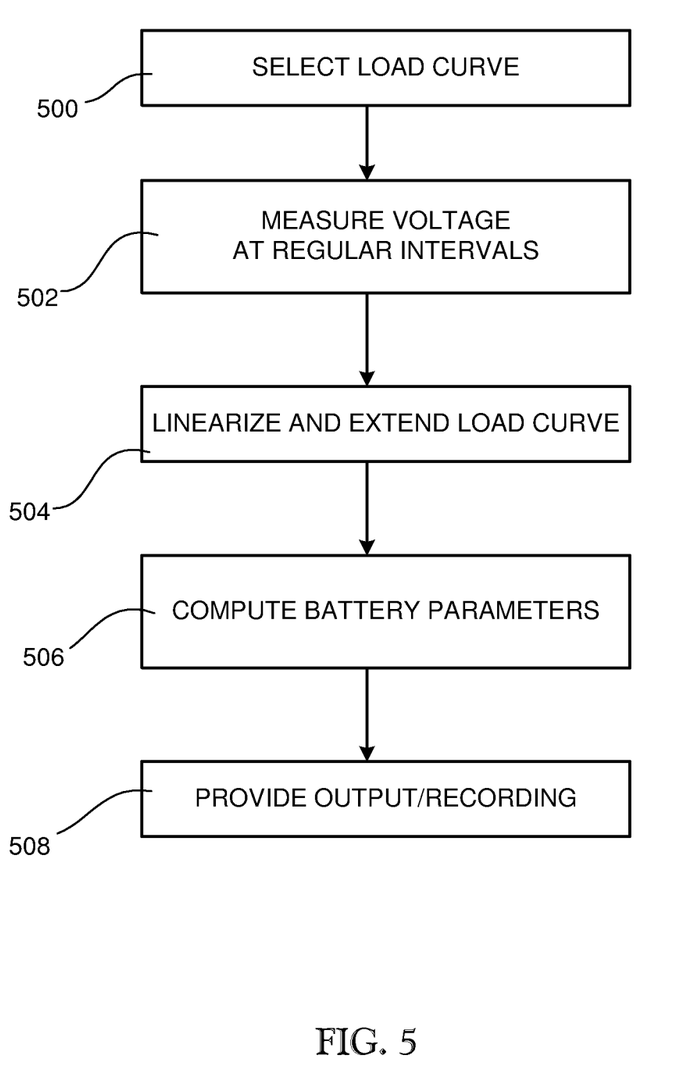
FIG. 5 is a flowchart outlining the steps in another embodiment of a method for estimating battery capacity in accordance with the present disclosure.

As noted above, the method outlined in FIG. 4 involves transmitting data, such as voltage measurements and battery life estimations, between an implanted device and an external device. However, all of the steps in the disclosed method can be performed by the implanted device, depending upon power availability and programming. Additionally, the overall method can be viewed in a more simplified way, as depicted in FIG. 5. Provided in FIG. 5 is a flowchart outlining the steps in a simplified embodiment of a method for estimating battery capacity in accordance with the present disclosure. As with the embodiment shown in FIG. 4, the first step is to select or establish an appropriate load curve (step 500), and can be done in the manner discussed above. Next, the system repeatedly measures battery terminal voltage at regular intervals (step 502). After each voltage measurement, the system linearizes and extends the load curve (step 504) in the manner outlined above, and computes the battery life parameters, such as time to IFI, NEOS, EOS and time to recharge (step 506). Finally, the system provides output of some kind to a user (step 508), indicating the battery life estimate, and records desired data, such as the voltage measurements, modified VDR curve, battery life estimates, etc. In one embodiment, where all operations are performed by an implanted device, output to a user can be in the form of an audible indication from the implanted device.

The method disclosed herein provides a simple and accurate battery useable time estimation. The accuracy of the time estimation increases over time for a given operating load or operational regime. No additional hardware is required to implement this method. Advantageously, this method allows battery energy to be used to the greatest extent possible, providing longer operating time or time between surgical operations to replace or service in implanted device. This method is accurate and independent of battery capacity, operating environment, load behavior, and dynamic and or static loads, etc. The method is independent because it does not need as many inputs as other battery estimation methods and adapts to changes during operation of the device. That is, if manufacturing variations or material flaws, or an intentional change in operating parameters, cause a given implanted device to consume more power than expected, this additional power demand will naturally change the voltage depletion rate, which will be reflected in the actual voltage measurements. Consequently, the system will automatically compensate for changes in electrical function of the device.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various vehicle components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A method for managing a battery powering an implantable medical device (IMD), comprising:
    obtaining a first plurality of voltage readings of the battery in the IMD;
    estimating future battery performance characteristics based upon a linear extrapolation from the first plurality of voltage readings;
    generating a first baseline curve of a voltage depletion over time for the battery in the IMD under selected operating parameters;
    generating a first estimate of future battery performance characteristics based upon the linear extrapolation from the first plurality of voltage readings and an initial point of the first baseline curve;
    modifying one or more operating parameters of the IMD;
    obtaining a second plurality of voltage readings of the battery in the IMD after modifying one or more operating parameters of the IMD and a delay period;
    generating a second baseline curve based upon the second plurality of voltage readings; and
    generating subsequent battery life estimates based upon the linear extrapolation of one or more subsequent voltage readings and the second baseline curve;
    wherein a length of the delay period reduces one or more errors in the second baseline curve.

2. The method in accordance with claim 1, wherein the performance characteristics include at least one of a time to depletion of the battery and a time to an end of service of the battery.

3. The method in accordance with claim 1, further comprising wirelessly transmitting data representing a detected terminal voltage of the battery from the IMD to a remote computing device.

4. The method in accordance with claim 3, wherein the IMD is an implantable pulse generator for vagus nerve stimulation.

5. The method in accordance with claim 3, wherein the steps of obtaining the first plurality of voltage readings and the second plurality of voltage readings are performed by the IMD; and the step of estimating future battery performance characteristics is performed by the remote computing device.

6. The method in accordance with claim 3, wherein the remote computing device is at least one of a PDA, a smartphone, a laptop computer, and a special purpose portable computing device.

7. The method in accordance with claim 1, further comprising providing an indication of the future battery performance characteristics.

8. The method in accordance with claim 7, wherein the indication is at least one of an indicator light, an alphanumeric display, an iconic indicator, and an audible indicator.

9. A method for estimating a life of a battery in an implantable medical device (IMD), comprising:
    obtaining a first baseline curve of a voltage depletion over time for the battery in the IMD under selected operating parameters;
    obtaining a first reading and subsequent readings of battery terminal voltage at regular intervals;
    generating a first battery life estimate based upon a linear extrapolation from the first voltage reading and the first baseline curve;
    modifying one or more operating parameters of the IMD;
    obtaining a plurality of voltage readings of the battery in the IMD after modifying one or more operating parameters of the IMD and a delay period;
    generating a second baseline curve based upon the plurality of voltage readings; and
    generating subsequent battery life estimates based upon the linear extrapolation of one or more subsequent readings of battery terminal voltage and the second baseline curve;

wherein a length of the delay period reduces one or more errors in the second baseline curve.

10. The method in accordance with claim 9, wherein the first battery life estimate includes at least one of a time to depletion of the battery and a time to an end of service of the battery.

11. The method in accordance with claim 9, wherein the regular intervals are about once per day.

12. The method in accordance with claim 9, further comprising providing an indication of the first battery life estimate or subsequent battery life estimates using an indicator including at least one of an indicator light, an alphanumeric display, an iconic indicator, and an audible indicator.

13. The method in accordance with claim 9, further comprising wirelessly transmitting data representing the voltage readings from the IMD to a remote computing device, wherein the steps of obtaining the first reading, the plurality of voltage readings, and subsequent readings of battery terminal voltage are performed by the IMD; and the steps of generating the first battery life estimate and subsequent battery life estimates are performed by the remote computing device.

14. The method in accordance with claim 13, wherein the remote computing device is at least one of a PDA, a smartphone, a laptop computer, and a special purpose portable computing device.

15. An implantable system, comprising:
an implantable device, having a microprocessor and system memory, a battery, and a battery circuit capable of measuring battery terminal voltage;
an external computing device, having a microprocessor and system memory; and
a computer program product, stored in the system memory of at least one of the implantable device and the external device, comprising machine-readable instructions for:
periodically measuring terminal voltage of the battery;
obtaining a first baseline curve of a voltage depletion over time for the battery in the IMD under selected operating parameters;
obtaining a first reading and subsequent readings of battery terminal voltage at regular intervals;
generating a first battery life estimate based upon a linear extrapolation from a first voltage reading and a first baseline curve;
modifying one or more operating parameters of the IMD;
obtaining a plurality of voltage readings of the battery in the IMD after modifying one or more operating parameters of the IMD and a delay period;
generating a second baseline curve based upon the plurality of voltage readings; and
generating subsequent battery life estimates based upon the linear extrapolation of one or more subsequent voltage readings and the second baseline curve;
wherein a length of the delay period reduces one or more errors in the second baseline curve.

16. The system in accordance with claim 15, wherein the system memory includes data representing the first baseline curve of voltage depletion over time for the battery in the implantable device under selected operating parameters, and the computer program product includes instructions for generating the first battery life estimate based upon the first baseline curve and a first of the periodic voltage measurements.

17. The system in accordance with claim 15, wherein the implantable device further comprises a wireless transmitter, and programming instructions for periodically measuring terminal voltage of the battery and transmitting data representative thereof to the external computing device.

18. The system in accordance with claim 15, wherein the external computing device is at least one of a PDA, a smartphone, a laptop computer, and a special purpose portable computing device.

19. The system in accordance with claim 15, wherein the external computing device includes an indicator mechanism including at least one of an indicator light, an alphanumeric display, an iconic indicator, and an audible indicator, the indicator mechanism being configured to providing to an indication of the battery life estimate.

20. The method in accordance with claim 1, wherein the operating parameters of the IMD comprise:
a signal amplitude;
a signal frequency;
a signal pulse width;
a signal on-time; and
a signal off-time.

21. The method in accordance with claim 1, wherein the delay period reduces errors in the second plurality of voltage readings.

22. The method in accordance with claim 9, wherein the operating parameters of the IMD comprise:
a signal amplitude;
a signal frequency;
a signal pulse width;
a signal on-time; and
a signal off-time.

* * * * *